United States Patent [19]
Korn

[11] Patent Number: 5,092,768

[45] Date of Patent: Mar. 3, 1992

[54] WIRE LIP BUMPER

[76] Inventor: Marcel Korn, 328 Newberry St., Boston, Mass. 02115

[21] Appl. No.: 687,335

[22] Filed: Apr. 18, 1991

[51] Int. Cl.$^5$ .............................................. A61C 3/00
[52] U.S. Cl. ......................................... 433/18; 433/20
[58] Field of Search ...................... 433/17, 18, 20, 21, 433/22, 5, 6, 7

[56] References Cited

U.S. PATENT DOCUMENTS

| | | | |
|---|---|---|---|
| 1,638,006 | 8/1927 | Aderer | 433/20 |
| 3,293,747 | 12/1966 | Denholtz | 433/21 |
| 4,764,112 | 8/1988 | Bergersen | 433/20 |
| 4,797,093 | 1/1989 | Bergersen | 433/5 |
| 4,881,896 | 11/1989 | Bergersen | 433/5 |
| 4,897,035 | 1/1990 | Green | 433/17 |

OTHER PUBLICATIONS

Rocky Mountain Orthodontics Catalog No. 40 (1973), p. 68.
Ormco Corporation brochure (1968).

Primary Examiner—Cary E. O'Connor
Attorney, Agent, or Firm—Lloyd L. Zickert

[57] ABSTRACT

A lip bumper formed solely of wire for applying forces to molars and which is U-shaped in form to include an arcuate segment aligned generally with the anterior teeth and substantially straight segments extending along the posterior teeth wherein the arcuate segment includes a plurality of loops defining an increased surface area engaging the lips so as to distribute the forces uniformly and provide greater patient comfort.

15 Claims, 1 Drawing Sheet

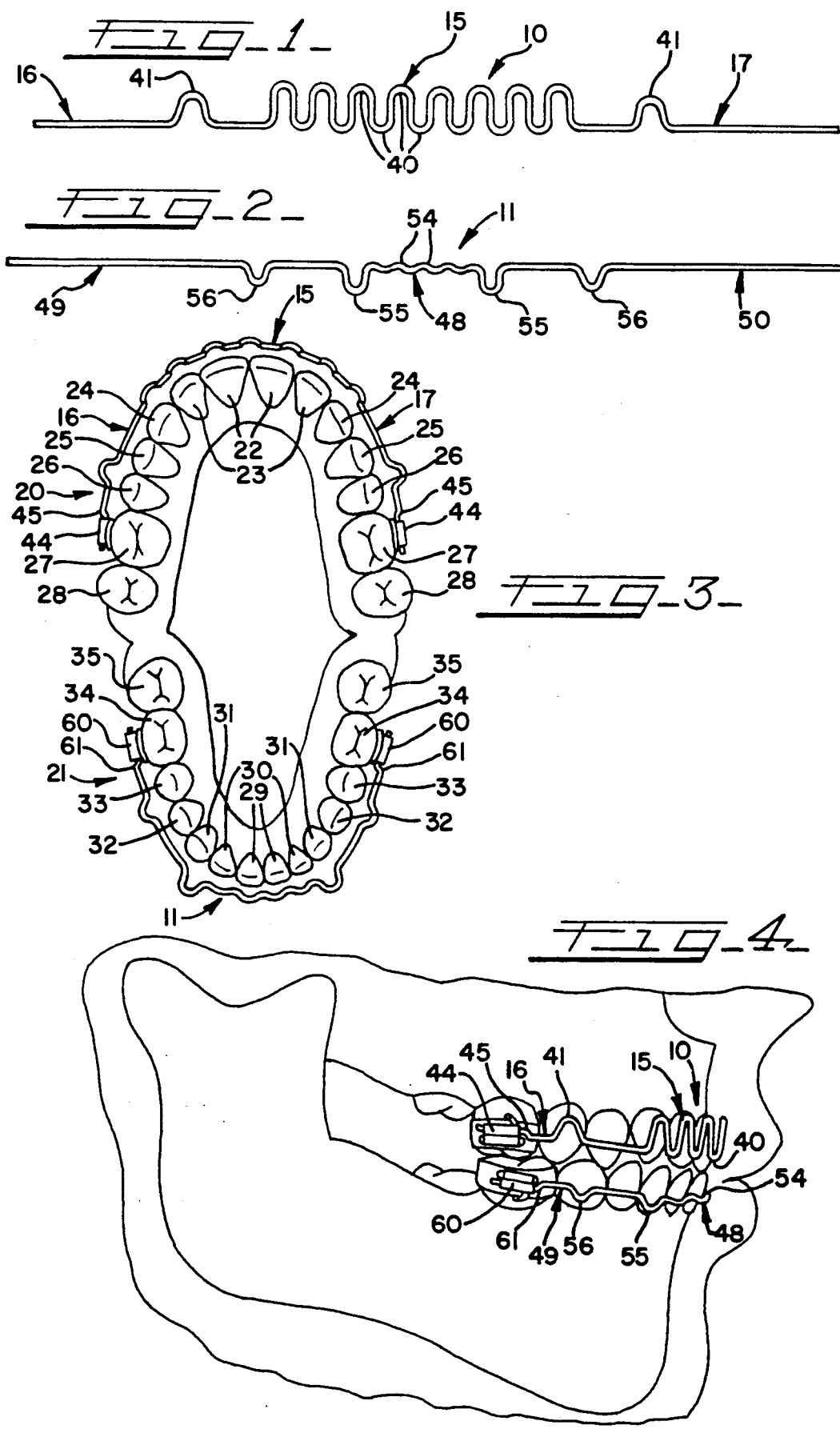

WIRE LIP BUMPER

This invention relates in general to lip bumpers, and more particularly to lip bumpers made solely of wire and which provide greater patient comfort and uniform force distribution to molars.

BACKGROUND OF THE INVENTION

Heretofore, it has been known to provide lip bumpers of various types wherein the lip bumpers are of wire. However, such lip bumpers are not only uncomfortable but may damage lip tissue wherein they inhibit patient cooperation.

Other prior known lip bumpers include acrylic pads along the wire which, while providing some comfort to the patient, are difficult to adjust, rigid and inflexible, require custom making to have proper fit, and are quite costly.

It has also been known to provide wire lip bumpers having plastic tubes fitting over the wire. Such bumpers are rigid and inflexible, tight-fitting into the buccal tubes, and the tubes become filled with contaminants and are unsightly.

SUMMARY OF THE INVENTION

The lip bumpers of the present invention overcome the prior known difficulties and are unique in that they are constructed to give better tissue tolerance and greater patient comfort which results in obtaining patient acceptance and compliance. They will function to simulate the buccal shields of the Frankel appliance, provide space maintenance and headgear functions, keep lips and cheeks away from the teeth to maintain post-palatal expansion, and rotate molars from the buccal. Further, the lip bumpers of the invention provide an increased surface area to engage the musculature of the lip more uniformly so as to distribute the forces of the lips more evenly to the molars. Moreover, the lip bumpers of the invention are constructed so that they may be easily adjusted during treatment.

The lip bumper of the invention is made solely of wire that includes a portion to align with the anterior teeth which has a plurality of loops that increase the surface area engaged by the lips. Being made solely of wire with open loops, it stays clean to enhance mouth hygiene. Because the lip bumper is made solely of wire, it is easy to adjust during treatment of a patient so that better results can ultimately be obtained. Moreover, the lip bumper of the invention is constructed to provide lighter forces as would be obtainable from the musculature of the lips, is more flexible, and fits more easily into the buccal tubes. The lip bumper transfers muscle forces to the molars to achieve the desired treatment effect.

More specifically, the lip bumper of the invention is capable of distalizing molars, rotating molars, and also uprighting molars, all by the application of light forces.

The lip bumper of the invention is inserted into molar tubes and provided with a stop to seat the bumper against the tubes so that it is in spaced relation from the teeth and will be acted on by the muscles of the lip.

It is therefore an object of the present invention to provide a new and improved lip bumper for applying relatively light forces to the molars of either arch and which is made solely of wire with multiple loops provided in the anterior portion of the bumper to define an increased surface area against which the lip will apply its forces.

Another object of the invention is in the provision of a new and improved lip bumper having a plurality of spaced apart loops formed along a wire body that engage the lip muscle and which provides greater patient comfort and subsequent greater patient acceptance and cooperation to use the bumper.

Another object of the invention is in the provision of a new and improved lip bumper made entirely of wire and having multiple loops at the area aligning with the anterior teeth to provide an increased surface area for the lip muscles and wherein the bumper has the ability to be easily adjusted during treatment.

A further object of the invention is to provide an improved lip bumper that is relatively flexible and loose-fitting in the buccal tubes, and capable of providing space maintenance and headgear functions.

A still further object of the invention resides in the provision of an improved lip bumper that will maintain post palatal expansion, and that will take advantage of rotation of molars from the buccal.

Another object of the invention is to provide an improved all-wire lip bumper that enhances the hygiene of the mouth.

Still another object of the invention is to provide improved upper and lower lip bumpers that simulate the buccal shields of a Frankel appliance in modular fashion where an upper, a lower or both may be used for a patient.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is an elevational view of a lip bumper according to the invention for use with respect to the upper arch and in the form prior to being adjusted for a particular patient;

FIG. 2 is an elevational view of a lip bumper of the invention for the lower arch and in the form prior to final adjustment for mounting in a patient's mouth;

FIG. 3 is an occlusal view of the upper and lower arches having the lip bumpers of FIGS. 1 and 2 mounted in place; and FIG. 4 is a side elevational view of the jaws of a person to illustrate the lip bumpers of the invention in mounted relation.

DETAILED DESCRIPTION OF THE INVENTION

It is known that lip bumpers are useful in applying forces to the molars for distalizing molars, rotation of molars, or uprighting of molars, depending upon the needs for a particular patient. For example, it has been known to use lip bumpers on patients having crowding malocclusions in the lower or mandibular arch. They can also be used in patients having Class III malocclusions in the upper or maxillary arch. Often, it is found in a Class II situation that the lower incisors are "pushed in" and/or a retrognathic mandible is presented. This is quite often due to a hyperactive mentalis muscle. The function of the mentalis muscle in the chin is to elevate the skin of the chin and turn the lower lip outward. It is considered to be a powerful muscle that can greatly influence normal or abnormal development of the lower denture. By using a lip bumper, the energy of the mentalis muscle can be harnessed and used for orthodontic treatment of the patient.

With respect to a lip bumper for the lower arch, it is inserted into 0.045 or 0.051 lower molar round tubes. The anterior portion of the bumper is positioned in the lower labial sulcus or around the gingival area of the lower. anteriors. It would be sized to be a few millimeters off the gingival tissue, and therefore it would be disposed between the teeth and the lip. Energy from the mentalis muscle is absorbed by the bumper and transferred to the lower molars which react accordingly. Because the bumper is positioned away from the teeth and the gingival tissue, the inhibiting mentalis muscle cannot interfere with normal development of the denture.

Lip bumper use can gain space in the arch by distalizing the molars or even by rotating and uprighting the molars, thereby eliminating the need for extraction of teeth. Where uprighting or rotating of the molars is obtained, posterior anchorage is developed for use in later obtaining anterior tooth movement. It will be appreciated that a patient may be treated with lip bumpers of the invention in a more satisfactory method because of the broader surface area defined for muscle function. By use of lip bumpers gentler forces are exerted to increase patient acceptance and response.

Referring now to the drawings, FIGS. 1 and 2 illustrate respectively upper and lower lip bumpers of the invention in the forms that they would be delivered to the orthodontist prior to adjusting for a particular patient and placing it with the patient. It will be appreciated that for a particular patient, a lip bumper on one or both of the arches may be used. Even they are illustrated in mounted position and use in FIGS. 3 and 4. For example, it may only be necessary to use a lip bumper for the upper arch of one patient or the lower arch of another patient, and in certain instances it will be preferable to use the lip bumper for both arches in tandem. In order to provide a true functioning system such as to approximate the functional appliance therapy as provided by appliances such as the Frankel appliance, lip bumpers of the invention can be used in tandem. They can also take the place of headgear which are designed to apply much greater forces to molars or they could be used to augment headgear by wearing in the daytime. Thus, the lip bumpers provide space maintenance and headgear functions, as well as maintain post palatal expansion. As above indicated, when using the lip bumpers of the invention in tandem, they mimic the buccal shields of Frankel appliances, thereby providing a functional effect within a fixed system. However, they may be modularly used where only an upper, a lower or both may be prescribed. The Frankel appliance, however, includes both upper and lower at all times.

The upper or maxillary lip bumper of the invention is generally designated by the numeral 10, while the lower or mandibular lip bumper is generally designated by the numeral 11. The lip bumper 10 generally includes a frontal or lip-engaging section 15 adapted to generally align with the anterior teeth when mounted in the patient's mouth and laterally arranged sections 16 and 17 which generally align with the posterior teeth and which extend distally to the molar tubes. For purposes of differentiating between the anterior and posterior teeth, the anterior teeth are generally considered to be from cuspid to cuspid and the teeth distally of the cuspids are considered to be the posterior teeth. It should be appreciated that some might limit the posterior teeth only to the centrals and laterals.

With respect to FIGS. 3 and 4, the upper arch is designated at 20 and the lower arch at 21. The upper arch includes centrals 22, laterals 23, cuspids 24, first bicuspids 25, second bicuspids 26, first molars 27, and second molars 28. Similarly, the lower arch includes opposing teeth that are defined as centrals 29, laterals 30, cuspids 31, first bicuspids 32, second bicuspids 33, first molars 34, and second molars 35. It will be understood that this is a typical arrangement of teeth and that in some patients certain teeth would have been extracted and sometimes the second molars are not in place at the time of treatment.

With respect to the upper lip bumper, the generally lip-engaging section 15 is aligned with the anterior teeth from cuspid to cuspid, while the segments 16 and 17 of the bumper are generally aligned along the posterior teeth distal to the cuspids. When mounted in the mouth, the lip-engaging section 15 is arcuately formed, while the buccal sections 16 and 17 are generally straight.

Both lip bumpers are made solely of wire with multiple open loops. The upper lip bumper 10 includes a plurality of side-by-side loops 40 at the lip-engaging section 15. The loops are generally U-shaped and alternate loops face respectively the gingival and the occlusal. The height of the loops is substantially equal to the height of the exposed labial area of the teeth or the crown of the teeth and the loops extend substantially between the cuspids. Moreover, the loops generally are disposed at a level above the level of the substantially straight sections 16 and 17. The loops are further sized to be close enough together to define a tissue-engaging area over a broad surface that will be comfortable to the patient and which will enhance tissue tolerance.

The lateral sections 16 and 17, while being generally straight, also include a single loop 41 that additionally serves to maintain the spacing of the cheeks from the teeth.

The distal ends of the lip bumper 10 are inserted into the buccal tubes 44 mounted on the first molars 27. These buccal tubes would have an opening sufficient to freely receive the distal ends of the lip bumper. Preferably, the lip bumper is made of 0.040 inch stainless steel wire for relatively loose fit into 0.045 inch buccal tubes. Insertion is therefore relatively easy to accomplish by the patient. Further, the use of 0.040 wire provides a less rigid and more flexible appliance. When mounting the lip bumper and adjusting it for a patient, stops will be bent into the distal ends of the sections 16 and 17, as indicated at 45, that would seat the bumper and maintain it in position between the teeth and the lips so that the lips could apply a force to the molars. As distalizing or uprighting or rotating is accomplished, adjustment may be made of the lip bumper in order to continue to have it in an active state if desired.

The lower lip bumper 11 according to the invention includes multiple loops that are of somewhat less amplitude in height than the height of the crowns of the lower teeth. The lip bumper 11 includes a lip-engaging section 48 which would be arranged in alignment with the anterior teeth and lateral sections 49 and 50. Preferably, the lower lip bumper's lip-engaging section would include a plurality of loops of normal amplitude and designated a loop 54 between larger loops 55. Again, loops would be provided in the lateral sections 49 and 50, such as loops 56. As above mentioned, the lip-engaging section 48 would be aligned with the anterior teeth, while the lateral sections 49 and 50 would be generally aligned with the posterior teeth. Again, the lip bumper 11 would be mounted in the mouth so that the distal ends of the sections 49 and 50 would be received in molar tubes 60 that are suitably mounted on the first molars 34. During adjustment of the lip bumper for a particular patient, stops 61 would be defined in the sections 49 and 50 so as to seat the lip bumper in the desired position between the teeth and the lips.

In view of the foregoing, it will be appreciated that the lip bumpers of the invention are unique in that they are made solely of wire and are provided with multiple open loops so that they can define broad lip-engaging areas that are comfortable to a patient and which will enhance patient comfort.

It will be understood that modifications and variations may be effected without departing from the scope of the novel concepts of the present invention, but it is understood that this application is to be limited only by the scope of the appended claims.

The invention is hereby claimed as follows:

1. A lip bumper appliance for the upper or lower arch mounted on molar tubes for applying forces to molars through action of the lips, said lip bumper being disposed between the lips and teeth and comprising a generally U-shaped wire form having distal ends received in said molar tubes, and a plurality of equally spaced apart open loops in the area of the anterior teeth, wherein the loops provide an enhanced area for musculature engagement to distribute the forces to the molars more uniformly.

2. The lip bumper of claim 1, wherein the loops include a vertical height that effectively defines a broader surface for muscle function.

3. The lip bumper of claim 2, where the wire is 0.040 inch round and thus tubes include 0.045 inch openings.

4. The lip bumper of claim 1, wherein the loops of the wire form extend substantially toward the gingival but are spaced from the teeth.

5. The lip bumper of claim 1, wherein the loops of the wire form extend substantially toward the occlusal.

6. A lip bumper appliance for an arch mounted on molar tubes attached to the molars and coacting with the lips for applying distal forces to the molars, said lip bumper being disposed around the arch and between the lips and teeth and including a substantially U-shaped wire body having a lip-engaging section and substantially straight sections along both sides of the arch, said straight sections adapted to be received in the molar tubes, stop means on the distal ends of the straight sections for seating the lip bumper in the tubes so that the lip-engaging section between the straight sections is off the teeth and engaged by the lip muscle, and a plurality of equally spaced apart open loops along the lip-engaging section extending gingivally from the level of the straight sections to provide an enhanced area for musculature engagement.

7. The lip bumper of claim 6, wherein the loops are U-shaped and include both gingival and occlusal extending segments and extend substantially along at least the centrals and laterals.

8. The lip bumper of claim 7, wherein the loops are of the same size.

9. The lip bumper of claim 7, wherein the loops are of different sizes.

10. The lip bumper of claim 7, wherein for the upper arch the loops are of a height substantially equal to the height of the exposed labial surfaces of the teeth.

11. The lip bumper of claim 7, wherein for the lower arch, the loops are of a height less than the height of the exposed labial surface of the teeth.

12. The lip bumper of claim 7, wherein the bumper is made of solely of wire.

13. The lip bumper of claim 6, wherein the loops are U-shaped and include both gingival and occlusal extending segments and extend substantially along the anterior teeth between the cuspids.

14. The lip bumper of claim 6, wherein the lip bumper is formed to be used on the upper arch.

15. The lip bumper of claim 6, wherein the lip bumper is formed to be used on the lower arch.

* * * * *